United States Patent [19]

Cho et al.

[11] Patent Number: 5,037,467
[45] Date of Patent: Aug. 6, 1991

[54] AMIDOXIME DERIVATIVES, USEFUL AS SELECTIVE HERBICIDE

[76] Inventors: Kwang Y. Cho, 383-21 Doryong-Dong; In H. Jeong, Kongdong-Kwanri Apt. 8-102, Doryong-Dong, both of Youseong-Ku, Daejeon; Young S. Kim, 167-7 Ryuchung-Dong; Beom T. Kim, Samseong Apt. 15-806, Oryu-Dong, both of Chung-Ku, Daejeon; Yong K. Min, 492-37 Yongwun-Dong, Dong-Ku, Daejeon; Geun S. Jeon, 706-22 Hoejadong, Chuncheon; Jin S. Kim, 262-37 Youngmun-Dong, Seo-Ku, Daejeon; Kyung S. Hong, Saejeong Apt. 10-403, Beop-Dong, Daedeog-Ku, Daejeon; In T. Hwang, 58-30 Gajang-Dong, Seo-Ku, Daejeon; Suk J. Koo, Chukong Apt. 153-21, Yongwun-Dong, Dong-Ku, Daejeon, all of Rep. of Korea

[21] Appl. No.: 373,794

[22] Filed: Jun. 29, 1989

[30] Foreign Application Priority Data

Feb. 26, 1988 [KR] Rep. of Korea ............... 1999/1988

[51] Int. Cl.$^5$ ............ A01N 33/08; A01N 33/16; C07C 69/96; C07D 265/30
[52] U.S. Cl. .................................... 71/87; 71/88; 71/106; 71/107; 71/111; 71/121; 544/162; 548/175; 548/262; 560/35; 564/229
[58] Field of Search ............... 544/162; 558/175, 262; 560/35; 564/229; 71/87, 88, 106, 107, 111, 121

[56] References Cited

U.S. PATENT DOCUMENTS 3,547,621 12/1970 Ralph et al. ...................... 71/121

OTHER PUBLICATIONS

Kim et al., Chem. Abstracts, vol. 102; 24541c (1985).

Primary Examiner—Johann Richter
Attorney, Agent, or Firm—Gifford, Groh, Sprinkle, Patmore and Anderson

[57] ABSTRACT

The present invention relates to amidoxime derivatives of the formula (I):

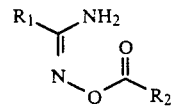

wherein $R_1$ is a $C_{1-3}$ alkyl or allyl group, a methyl group substituted by chlorine or fluorine atom or ethoxycarbonyl or diethyldithiophosphate group, a phenoxymethyl group unsubstituted or substituted by chlorine atom, a $C_2$ alkoxy or phenoxy group unsubstituted or substituted by chlorine atom or ethoxycarbonylethoxy group, a phenyl group unsubstituted or substituted by chlorine or fluorine atom, a benzyl group unsubstituted or substituted by chlorine atom, or a morpholine group; $R_2$ is a phenoxymethyl or phenoxyethyl group substituted by chlorine atom, a phenyl group substituted by chlorine atom or methoxy group, or an ethoxy group. The compounds of the invention have a extremely high selectivity between paddy rice or crop plants and weeds and a strong activity on weeds. Moreover, the compounds have a very low phytotoxicity to paddy rice and crop plants.

3 Claims, No Drawings

AMIDOXIME DERIVATIVES, USEFUL AS SELECTIVE HERBICIDE

BACKGROUND OF THE INVENTION

1. Field of the Invention

The present invention relates to the new amidoxime derivatives having an excellent herbicidal activity, method for preparation therefor and the herbicidal composition comprising it.

2. Description of the Invention

Phenoxy type herbicides such as 2,4-D, 2,4,5-T, MCPA and MCPB have been employed as post-emergence application to control paddy and upland weeds. Since the phenoxy type herbicides cause the severe phytotoxicity to paddy rice and crop plants depending on the timing of application or the weather conditions, it has been strongly desired to develop a new type of herbicide which is able to overcome the phytotoxicity on paddy rice and crop plants and control annual and perennial weeds in paddy and upland field. In other words, a new type of herbicide should have a extremely high selectivity between paddy rice or crop plants and weeds and a strong activity on weeds.

SUMMARY OF THE INVENTION

Under the above circumstances, the present inventors conducted intensive studies for developing herbicides having low phytotoxicity to paddy rice and crop plants and high selectivity between paddy rice or crop plants and weeds. They found that amidoxime derivative of the following formula(I) has low phytotoxicity, high selectivity and strong activity.

Accordingly, it is an object of the invention to provide a new type of herbicide which can industrially be produced and which is able to control annual and perennial weeds in paddy and upland field with keeping high selectivity between crops and weeds.

DETAILED DESCRIPTION OF THE INVENTION

The present invention relates to amidoxime derivatives of the formula(I)

$$R_1-\underset{N-O}{\overset{NH_2}{C}}-\overset{O}{\underset{}{C}}-R_2$$

wherein $R_1$ represents a $C_{1-3}$ alkyl or allyl group, a methyl group substituted by chlorine or fluorine atom or ethoxycarbonyl or diethyldithiophosphate group, a phenoxymethyl group unsubstituted or substituted by chlorine atom, a $C_2$ alkoxy or phenoxy group unsubstituted or substituted by chlorine atom or ethoxycarbonylethoxy group, a phenyl group unsubstituted or substituted by chlorine or fluorine atom, a benzyl group unsubstituted or substituted by chlorine atom, or a morpholine group; $R_2$ represents a phenoxymethyl or phenoxyethyl group substituted by chlorine atom, a phenyl group substituted by chlorine atom or methoxy group, or an ethoxy group.

The compounds of formula(I) of this invention can be prepared, for example, by the following process:

$$R_1-\underset{}{\overset{OH}{\underset{}{C}}}-NH_2 + Cl\overset{O}{\underset{}{C}}-R_2 \longrightarrow R_1-\underset{N-O}{\overset{NH_2}{C}}-\overset{O}{\underset{}{C}}-R_2$$
(II)      (III)                    (I)

wherein $R_1$ and $R_2$ have the same meaning as defined above.

In other words, the compound(I) of this invention can be prepared by reacting the compound(II) with acylchloride of the compound(III).

The above reaction is carried out at room temperature in the presence of a base for 1 to 5 hours. Various solvents can be used in this reaction, which include acetone, acetonitrile, toluene, ethylacetate, methylene chloride, ether, dioxane, etc. For the base, they may be employed triethylamine, pyridine, sodium carbonate, potassium carbonate, etc.

After the reaction is completed, the objective products are separated from the reaction mixture and purified according to a conventional method. For instance, the reaction mixture is washed with water, followed by distillation of the solvent, and the residue being purified by chromatography to obtain a compound(I) at a high yield.

EXAMPLES

Now, the present invention will be described in further detail with reference to the following examples. However it should be understood that the present invention is by no means restricted to these specific examples.

Example 1

O-(2,4-dichlorophenoxy)acetylchloroacetamidoxime: compound No. 2

2.17 g of chloroacetamidoxime, 4.79 g of 2,4-dichlorophenoxyacetyl chloride and 2.02 g of triethylamine were added to 50 ml of toluene. The mixture was stirred at room temperature for 1 hour. After completion of the reaction, the mixture was washed with 100 ml of water and then toluene was distilled off, and the residue was purified by column chromatography using a mixture of solvent (benzene:ether=4:1) to obtain 5.92 g of the desired compound (yield: 95.1%).

Typical examples of the compounds obtained are shown in Table 1 with their physical properties.

TABLE 1

$$R_1-\underset{NH_2}{C}=N-O-\underset{O}{\overset{\|}{C}}-R_2$$

| Compound No. | $R_1$ | $R_2$ | Physical properties | Element analysis (%) Calculated value (Measured value) C | H | N | NMR (δ, ppm) |
|---|---|---|---|---|---|---|---|
| 1 | $CH_3CH_2CH_2-$ | $-CH_2O-\text{(2,4-diClC}_6\text{H}_3\text{)}$ | mp 96–97° C. | 47.23 (47.31) | 4.62 (4.65) | 9.18 (9.23) | 7.15–6.65(m,3H), 4.80(bs,2H), 4.75(s,2H), 2.05(t,2H), 1.53(m,2H), 0.91(t,3H) |
| 2 | $FCH_2-$ | $-CH_2O-\text{(2,4-diClC}_6\text{H}_3\text{)}$ | mp 94–96° C. | 40.69 (40.57) | 3.05 (3.01) | 9.49 (9.56) | 7.55–7.00(m,3H), 6.45(bs,2H), 5.05(s,2H), 4.92(d,2H) |
| 3 | $ClCH_2-$ | $-CH_2O-\text{(2,4-diClC}_6\text{H}_3\text{)}$ | mp 92–93° C. | 38.55 (38.61) | 2.91 (2.96) | 8.99 (9.04) | 7.30–6.80(m,3H), 6.20(bs,2H), 4.90(s,2H), 4.10(s,2H) |
| 4 | $CH_2=CHCH_2-$ | $-CH_2O-\text{(2,4-diClC}_6\text{H}_3\text{)}$ | mp 99–100° C. | 47.55 (47.62) | 3.99 (3.92) | 9.24 (9.32) | 7.40–6.80(m,3H), 6.50–6.01(m,1H), 5.90–5.70(m,2H), 5.60(bs,2H)4.85(s,2H), 3.10–2.90(m,2H) |
| 5 | $C_6H_5OCH_2-$ | $-CH_2O-\text{(2,4-diClC}_6\text{H}_3\text{)}$ | mp 114–115° C. | 52.05 (52.13) | 3.82 (3.78) | 7.59 (7.54) | 7.40–6.80(m,8H), 6.40(bs,2H), 4.85(s,2H), 4.50(s,2H) |
| 6 | $CH_3CH_2O\underset{O}{\overset{\|}{C}}CH_2-$ | $-CH_2O-\text{(2,4-diClC}_6\text{H}_3\text{)}$ | mp 86–87° C. | 44.72 (44.81) | 4.04 (4.11) | 8.02 (8.13) | 7.20–6.60(m,3H), 5.45(bs,2H), 4.73(s,2H), 4.05(q,2H), 3.17(s,2H), 1.22(t,3H) |

TABLE 1-continued $$R_1\underset{\underset{N}{\|}}{\overset{NH_2}{C}}\underset{O}{\overset{}{\underset{}{-}}}\underset{O}{\overset{\|}{C}}-R_2$$

| Compound No. | $R_1$ | $R_2$ | Physical properties | Element analysis (%) Calculated value (Measured value) | | | NMR (δ, ppm) |
|---|---|---|---|---|---|---|---|
| | | | | C | H | N | |
| 7 | (C$_2$H$_5$O)$_2$P(S)SCH$_2$— | 2,4-diCl-phenyl-OCH$_2$— | mp 69–70° C. | 36.45 (36.51) | 4.15 (4.22) | 6.07 (6.14) | 7.40–6.70(m,3H), 5.35(bs,2H), 4.80(s,2H), 4.40–4.05(m,4H), 3.65(d,2H), 1.37(t,6H) |
| 8 | C$_6$H$_5$O— | 2,4-diCl-phenyl-OCH$_2$— | mp 167–168° C. | 50.73 (50.81) | 3.41 (3.48) | 7.89 (7.93) | 7.40–6.90(m,8H), 6.50(bs,2H), 4.80(s,2H) |
| 9 | 4-Cl-C$_6$H$_4$O— | 2,4-diCl-phenyl-OCH$_2$— | mp 132–133° C. | 46.24 (46.17) | 2.85 (2.92) | 7.19 (7.23) | 7.40–6.80(m,7H), 6.50(bs,2H), 4.85(s,2H) |
| 10 | CH$_3$CH$_2$O— | 2,4-diCl-phenyl-OCH$_2$— | mp 107–108° C. | 43.02 (43.11) | 3.94 (3.89) | 9.11 (9.21) | 7.30–6.70(m,3H), 4.70(s,2H), 4.70–4.30(bs,2H), 4.10(q,2H), 1.35(t,3H) |
| 11 | C$_2$H$_5$OC(O)CH(CH$_3$)O-C$_6$H$_4$-O— | 2,4-diCl-phenyl-OCH$_2$— | mp 117–118° C. | 50.97 (50.80) | 4.28 (4.22) | 5.94 (6.02) | 7.51–6.73(m,7H), 6.25(bs,2H), 5.02–4.62(m,3H), 4.18(q,2H), 1.51(d,3H), 1.18(t,3H) |

TABLE 1-continued

Structure:
$R_1-C(NH_2)=N-O-C(=O)-R_2$

| Compound No. | $R_1$ | $R_2$ | Physical properties | Element analysis (%) Calculated value (Measured value) | | | NMR (δ, ppm) |
|---|---|---|---|---|---|---|---|
| | | | | C | H | N | |
| 12 | $Cl_3C-$ | 2,4-dichloro-phenyl with $-CH_2O-$ linkage | mp 109–111° C. | 31.56 (31.47) | 1.84 (1.80) | 7.36 (7.47) | 7.65–7.00(m,3H), 5.95(bs,2H), 4.85(s,2H) |
| 13 | $CH_3CH_2CH_2-$ | 2,5-dichloro-3-methyl-phenyl ($CH_3O$) | oil | 47.23 (47.12) | 4.62 (4.58) | 9.18 (9.27) | 7.29–6.87(m,2H), 5.11(bs,2H), 3.78(s,3H), 2.21(t,2H) 1.62(m,2H), 0.97(t,3H) |
| 14 | $C_2H_5OCH_2CH_2-$ | 2,5-dichloro-3-methyl-phenyl ($CH_3O$) | mp 90–91° C. | 46.58 (46.67) | 4.81 (4.78) | 8.36 (8.39) | 7.30–6.84(m,2H), 5.30(bs,2H), 3.76(s,3H), 3.64–3.20(m,4H), 2.39(t,2H), 1.05(t,3H) |
| 15 | 2,4-dichlorobenzyl ($-CH_2-$) | 2,5-dichloro-3-methyl-phenyl ($CH_3O$) | mp 122–123° C. | 45.52 (45.44) | 2.87 (2.89) | 6.64 (6.58) | 7.30–6.89(m,5H), 4.96(bs,2H), 3.76(s,3H), 3.54(s,2H) |
| 16 | $CH_3-$ | 2,5-dichloro-3-methyl-phenyl ($CH_3O$) | oil | 43.34 (43.17) | 3.64 (3.59) | 10.11 (10.22) | 7.30–6.91(m,2H), 5.21(bs,2H), 3.76(s,3H), 1.90(s,3H) |

TABLE 1-continued structure: $R_1-C(NH_2)=N-O-C(=O)-R_2$

| Compound No. | R₁ | R₂ | Physical properties | Element analysis (%) Calculated value (Measured value) C | H | N | NMR (δ, ppm) |
|---|---|---|---|---|---|---|---|
| 17 | 2,4-dichlorophenyl-OCH₂– | 2,6-dichloro-3-methyl-methoxyphenyl (Cl, Cl, CH₃, OCH₃) | mp 113–114° C. | 43.86 (43.72) | 2.76 (2.74) | 6.40 (6.45) | 7.31–6.84(m,5H), 5.08(bs,2H), 4.70(s,2H), 3.76(s,3H) |
| 18 | 2,4-dichlorophenyl-CH₃ (methyl substituted dichlorophenyl) | 2,6-dichloro-3-methyl-methoxyphenyl | mp 150–151° C. | 44.15 (44.22) | 2.47 (2.46) | 6.87 (6.82) | 7.31–6.80(m,5H), 5.17(bs,2H), 3.76(s,3H) |
| 19 | 2,6-difluoro-methylphenyl | 2,6-dichloro-3-methyl-methoxyphenyl | mp 143–144° C. | 48.02 (48.13) | 2.69 (2.74) | 7.47 (7.42) | 7.42(m,5H), 5.21(bs,2H) 3.76(s,3H) |
| 20 | morpholino | 2,6-dichloro-3-methyl-methoxyphenyl | mp 115–116° C. | 44.84 (44.76) | 4.34 (4.30) | 12.07 (12.14) | 7.30–6.91(m,2H), 4.99(bs,2H), 3.80–3.61(m,7H), 2.99–2.80 (m,4H) |
| 21 | phenyl-CH₂– | 4-chlorophenyl-CH(CH₃)- | mp 142–144° C. | 61.35 (61.22) | 5.15 (5.23) | 8.42 (8.55) | 7.60–7.20(m,9H), 5.80(bs,2H), 4.60–4.20(q,1H), 3.45(s,2H), 1.80–1.60(d,3H) |

TABLE 1-continued $$R_1-C(NH_2)=N-O-C(=O)-R_2$$

| Compound No. | $R_1$ | $R_2$ | Physical properties | Element analysis (%) Calculated value (Measured value) | | | NMR (δ, ppm) |
|---|---|---|---|---|---|---|---|
| | | | | C | H | N | |
| 22 | phenyl | -CH(CH₃)-O-(4-Cl-phenyl) | mp 134–135° C. | 60.29 (60.38) | 4.74 (4.82) | 8.79 (8.62) | 7.50–7.20(m,9H), 5.80(bs,2H), 4.60–4.30(q,1H), 1.90–1.70 (d,3H) |
| 23 | 2-chlorophenyl | -CH(CH₃)-O-(4-Cl-phenyl) | mp 147–148° C. | 54.41 (54.37) | 3.99 (4.07) | 7.93 (7.98) | 7.60–7.10(m,8H), 5.90(bs,2H), 4.60–4.20(q,1H), 1.80–1.60 (d,3H) |
| 24 | 2,4-dichloro-6-(OCH₂–)phenyl | —OCH₂CH₃ | mp 122–124° C. | 43.02 (43.07) | 3.94 (3.89) | 9.12 (9.07) | 7.25–7.01(m,3H), 6.30(bs,2H), 4.50(s,2H), 4.40–4.02(q,2H), 1.50–1.15(t,3H) |

The compounds of the present invention may be used as they are but normally they are used in the form of such as wettable powders, dusts, emulsion concentrates, suspension concentrates, or may be used after dilution with water.

When liquid formulations are applied, the solvent such as water, alcohol, ether, acetone, ester, amide or petroleum ether may be used. As the solid carrier, an inorganic powder such as magnesium lime, gypsum, calcium carbonate, silica, alumina, zeolite, clay mineral and resin powder may be used.

The dosage of the present invention to be used as an active ingredient may be varied depending on the type of formulation, the manner for application, the timing and the weather condition. The dosage is usually varied in a range of 0.25 to 4 Kg/ha.

The compounds of the present invention are sufficiently effective even if they are applied solely. However, their application in combination with one or more types of compounds having herbicidal activity makes a possibility not only reduce the amount of the active ingredient, but also attain the enlargement of the herbicidal spectrum or improve the effects.

The typical examples of herbicides that can be used together with the compounds of the present invention are mentioned, for example, amide - type herbicides such as monalide, propanil, solan, diphenamide, fluoridamide, mefluidine, benzamizole, butachlor and alachlor; dinitroaniline - type herbicides such as trifluralin, benfluralin, profluralin, isopropaline, pendimenthalin and ethalfluralin; urea - type herbicides such as buturon, monolinuron, parafluron, tetrafluron, linuron, sulfodiazol, buthiuron, chlorosulfuron and sulfomethuronmethyl; carbamate - type herbicides such as chlorobufam, barban, diallate, phenmedipham, butylate, triallate, bentiocarb and methylbencarb; diphenylether - type herbicides such as oxyfluorofen, acifluorfornethyl, lactofen, formesafen and fluoronitrofen; and diazine - type herbicides such as oxadiazon and immazaquim.

Formulation Examples

Some examples of the formulations are given below.

Formulation Example 1 (Emulsion concentrate)

30 parts of compound No. 2 of the present invention, 60 parts of m-xylene and 10 parts of surfactant mixture(polyoxyethylene alkyl aryl ether and sodium alkyl aryl sulfate) were uniformly mixed and stirred to obtain an emulsion concentrate.

Formulation Example 2 (Wettable powder)

10 parts of compound No. 10 of the present invention, 85 parts of white carbon and 5 parts of surfactant mixture(polyoxyethylene alkyl aryl ether sulfate and polyoxyethylene alkyl and aryl ether) were mixed and pulverized to obtain a wettable powder.

Formulation Example 3. (Granule)

3 parts of compound No. 4 of the present invention, 60.0 parts of bentonite, 35 parts of talc, 0.5 parts of sodium dodecyl benzene sulfonate, 0.5 parts of sodium metasilicate and 1.5 parts of sodium tripolyphosphate were mixed, and after an addition of a proper amount of water, kneaded. The mixture was granulated by using an extrusion granulating machine and dried by a conventional method to obtain granules.

TEST EXAMPLES

Test example 1

Herbicidal test against paddy field weeds.

Paddy field soil was filled in 140 cm² plastic pot and irrigated. Paddy rice seedlings (Variety: Dongjin) of 2.5 leaf stage were transplanted and some amounts of paddy field weeds were also sown. On the second day after the transplantation, a predetermined amounts of the compound of the present invention was applied in the form of wettable powder.

During the test period, 2 cm in height of water from the surface of soil in the pot was maintained. Upon twentieth day after the treatment with compound of the present invention, the herbicidal effects against the weeds and phytotoxicity against paddy rice plants were examined. The results are shown in table 2 and herbicide rating system is shown in table 4.

TABLE 2

| Compound NO. | ORYSA | ECHOR | SCPJU | BR.s | ANEKE | MOOVA | CYPDI | CYPSE | SAGPY |
|---|---|---|---|---|---|---|---|---|---|
| 1 | 50 | 95 | | | 100 | 100 | 100 | | |
| 2 | 30 | 100 | 100 | 100 | | | | 100 | 100 |
| 3 | 40 | 100 | 100 | | 100 | 90 | 100 | | |
| 4 | 40 | 100 | 100 | | 100 | 100 | 100 | | |
| 5 | 60 | 100 | 100 | | 100 | 100 | 100 | | |
| 6 | 40 | 90 | 100 | | 100 | 100 | 100 | | |
| 7 | 60 | 100 | 100 | | 100 | 100 | 100 | | |
| 8 | 80 | 100 | 100 | | 100 | 100 | 100 | | |
| 9 | 50 | 100 | | | 100 | 100 | 100 | | |
| 10 | 80 | 100 | 100 | | 100 | 100 | 100 | | |
| 11 | 60 | 100 | 80 | 90 | | | | 80 | 100 |
| 12 | 60 | 80 | 90 | 100 | | | | 50 | 100 |
| 13 | 70 | 100 | 90 | 100 | | | | 100 | 80 |
| 14 | 70 | 100 | 100 | 100 | | | | 100 | 20 |
| 15 | 70 | 100 | 90 | 100 | | | | 100 | 50 |
| 16 | 80 | 100 | 100 | 100 | | | | 100 | 90 |
| 17 | 80 | 100 | 100 | 100 | | | | 100 | 90 |
| 18 | 80 | 100 | 100 | 100 | | | | 100 | 90 |
| 19 | 80 | 100 | 100 | 100 | | | | 100 | 90 |
| 20 | 80 | 100 | 100 | 100 | | | | 100 | 90 |
| 21 | 50 | 60 | | | 100 | 100 | 100 | | |
| 22 | 40 | 60 | | | 100 | 90 | 80 | | |
| 23 | 50 | 60 | | | 90 | 90 | 80 | | |

4 kg/ha

TABLE 2-continued

| Compound NO. | ORYSA | ECHOR | SCPJU | BR.s | ANEKE | MOOVA | CYPDI | CYPSE | SAGPY |
|---|---|---|---|---|---|---|---|---|---|
| | | | | | | | 4 kg/ha | | |
| 24 | 70 | 100 | 100 | | 100 | 100 | 100 | | |

*BR.s: mixture of annual broad leaf weeds such as ANEKE (dayflower), MOOVA (monochoria), ROTIN (toothcup) etc.

| PADDY WEED SPECIES | | |
|---|---|---|
| ABRV. | GENUS-SPECIES NAME | ENGLISH NAME |
| ORYSA | *Oryza sativa* L. | Rice |
| ECHOR | *Echinochloa curs-galli* P. BEAUV. var. oryzicola OHWI | Barnyardgrass |
| SCPJU | *Scirpus juncoides* ROXB. | Bulrush |
| CYPDI | *Cyperus difformis* L. | Umbrellaplant |
| CYPSE | *Cyperus serotinus* ROTTB. | Flat-sedge |
| ANEKE | *Aneilema keisak* HASSK. | Dayflower |
| MOOVA | *Monochoria vaginalis* PRESL. | Monochoria |
| ROTIN | *Rotala indica* KOEHE. | Toothcup |
| SAGPY | *Sagittaria pygmaea* MIQ. | Arrow head |

Test Example 2

Herbicidal test against upland weeds.

Alluvial soil was filled in 350 cm² plastic pot. Seeds of 10 weed species and seeds of corn, wheat, soybean, tomato and orchardgrass were sown and covered with soil. The pot was kept in a greenhouse. A test compound was formulated into an emulsion concentrate and diluted with water. A determined amounts of the compounds of the present invention was sprayed on the soil or over the leaves and stems of the plants by means of a small size spraying machine. The herbicidal effects against the weeds and the phytotoxicity of the crop plants were evaluated upon expiration of 2 to 3 weeks from the application. The results are shown Table 3 and herbicide rating system is shown in Table 4.

TABLE 3

PRE-Emergence 0.5 kg/ha

| Compound NO. | UPLAND WEED SPECIES | | | | | | | | | | |
|---|---|---|---|---|---|---|---|---|---|---|---|
| | LYPES | TRZAW | GLXMX | ZEAMX | DACGL | AMAVI | DIGSA | RUMJA | POLHY | AESIN | CAGHE |
| 1 | 90 | 40 | 90 | 20 | 70 | 100 | 100 | 60 | 40 | 60 | 100 |
| 2 | 100 | 60 | 70 | 60 | 90 | 100 | 100 | 90 | 80 | 100 | 100 |
| 3 | 100 | 55 | 65 | 55 | 90 | 100 | 100 | 90 | 75 | 100 | 100 |
| 4 | 90 | 20 | 70 | 30 | 70 | 100 | 100 | 80 | 60 | 80 | 100 |
| 5 | 90 | 50 | 60 | 40 | 80 | 100 | 80 | 40 | 30 | 40 | 100 |
| 6 | 80 | 45 | 60 | 20 | 70 | 100 | 90 | 40 | 60 | 60 | 100 |
| 7 | 50 | 30 | 65 | 20 | 60 | 95 | 60 | 30 | 30 | 50 | 100 |
| 8 | 75 | 10 | 65 | 40 | 70 | 100 | 90 | 30 | 55 | 40 | 100 |
| 9 | 50 | 20 | 60 | 40 | 50 | 100 | 80 | 10 | 60 | 80 | 100 |
| 10 | 90 | 40 | 70 | 40 | 40 | 100 | 95 | 40 | 50 | 80 | 100 |
| 11 | 90 | 20 | 60 | 10 | 40 | 100 | 80 | 10 | 10 | 0 | 0 |
| 12 | 90 | 50 | 80 | 20 | 80 | 100 | 100 | 80 | 80 | 90 | 100 |
| 13 | 100 | 95 | 100 | 60 | 80 | 100 | 100 | 100 | 100 | 100 | 100 |
| 14 | 100 | 100 | 100 | 70 | 100 | 100 | 100 | 100 | 100 | 100 | 100 |
| 15 | 100 | 100 | 100 | 70 | 90 | 100 | 100 | 100 | 100 | 100 | 100 |
| 16 | 100 | 90 | 100 | 60 | 80 | 100 | 100 | 100 | 100 | 100 | 100 |
| 17 | 100 | 80 | 100 | 60 | 70 | 100 | 100 | 90 | 100 | 100 | 100 |
| 18 | 100 | 80 | 100 | 60 | 70 | 100 | 80 | 100 | 100 | 100 | 100 |
| 19 | 100 | 80 | 100 | 60 | 100 | 100 | 100 | 90 | 100 | 100 | 100 |
| 20 | 100 | 80 | 100 | 60 | 90 | 100 | 100 | 100 | 100 | 100 | 100 |
| 21 | 100 | 50 | 65 | 50 | 0 | 70 | 70 | 80 | 80 | 70 | 80 |
| 22 | 60 | 30 | 30 | 0 | 0 | 65 | 70 | 65 | 70 | 80 | 85 |
| 23 | 20 | 0 | 0 | 0 | 30 | 70 | 65 | 70 | 75 | 85 | 40 |
| 24 | 30 | 0 | 40 | 30 | 50 | 100 | 95 | 10 | 0 | 20 | 100 |

| Compound No. | PADDY WEED SPECIES | | | |
|---|---|---|---|---|
| | ORYSA | ECHOR | CYPDI | ANEKE |
| 1 | 100 | 70 | 100 | 100 |
| 2 | 100 | 90 | 100 | 100 |
| 3 | 100 | 85 | 100 | 100 |
| 4 | 100 | 95 | 100 | 100 |
| 5 | 100 | 95 | 90 | 100 |
| 6 | 100 | 90 | 85 | 100 |
| 7 | 100 | 95 | 60 | 100 |
| 8 | 95 | 75 | 80 | 100 |
| 9 | 100 | 75 | 80 | 100 |
| 10 | 100 | 70 | 90 | 100 |
| 11 | 90 | 70 | 70 | 80 |
| 12 | 90 | 20 | 20 | 100 |
| 13 | 80 | 30 | 90 | 100 |
| 14 | 100 | 40 | 50 | 90 |
| 15 | 90 | 0 | 70 | 50 |
| 16 | 90 | 80 | 100 | 100 |
| 17 | 90 | 80 | 100 | 100 |
| 18 | 80 | 70 | 100 | 100 |
| 19 | 90 | 90 | 100 | 100 |
| 20 | 90 | 80 | 100 | 100 |
| 21 | 70 | 65 | 80 | 100 |

TABLE 3-continued

|   | PRE-Emergence 0.5 kg/ha | | | |
|---|---|---|---|---|
| 22 | 45 | 60 | 60 | 85 |
| 23 | 40 | 60 | 30 | 75 |
| 24 | 10 | 20 | 30 | 60 |

TEST PLANT FOR HERBICIDE EVALUATION

| ABRV. | GENUS-SPECIES NAME | ENGLISH NAME |
|---|---|---|
| UPLAND SPECIES | | |
| LYPES | Lycopersicon esculentum MILL. | Tomato |
| TRZAW | Triticum aestivum L. | Wheat |
| GLXMX | Glycine max (L.) MERR. | Soybean |
| ZEAMX | Zea mays L. | Corn |
| DACGL | Dactylis glomerata L. | Orchard grass |
| AMAVI | Amaranthus viridis L. | Pigweed |
| DIGSA | Digitaria sanguinalis (L.) SCOP. | Large crabgrass |
| RUMJA | Rumex japonicus HOUTT. | Dock |
| AESIN | Aeschynomene indica L. | Indian jointvetch |
| CAGHE | Calystegia japonica CHOISY | Bindweed |
| POLHY | Polygonum hydropiper L. | Smartweed |
| COMCO | Commelina communis L. | Common dayflower |
| PADDY SPECIES | | |
| ORYSA | Oryza sativa L. | Rice |
| ECHOR | Echinochloa crus-galli P.BEAUV. var. oryzicola OHWI | Barnyard-grass |
| CYPDI | Cyperus difformis L. | Umbrella-plant |
| ANEKE | Aneilema keisak HASSK. | Dayflower |

TABLE 4

Herbicide Rating System

| Rating Percent Control | Description of Main categories | Crop Description | Weed Description |
|---|---|---|---|
| 0 | No effect | No crop reduction or injury | No weed control |
| 10 | | Slight discoloration or stunting | Very poor weed control |
| 20 | Slight effect | Some discoloration, stunting or stand loss | Poor weed control |
| 30 | | Crop injury more pronounced but not lasting | Poor to deficient weed control |
| 40 | | Moderate injury, crop usually recovers | Deficient weed control |
| 50 | Moderate effect | Crop injury more lasting, recovery | Deficient to moderate weed control |
| 60 | | Lasting crop inury no recovery | Moderate weed control |
| 70 | | Heavy injury and stand loss | Control somewhat less than satisfactory |
| 80 | Severe effect | Crop nearly destroyed a few survivors | Satisfactory to good weed control |
| 90 | | Only occasional live plants left | Very good to excellent control |
| 100 | Complete effect | Complete crop destruction | Complete weed destruction |

What is claimed is:

1. An amidoxime derivative of the formula(I)

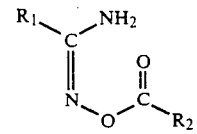

wherein $R_1$ represents fluromethyl, trichloromethyl, ethoxycarbonylmethyl, diethoxythiophosphonylthiomethyl, phenoxymethylethoxyethyl, allyl, phenoxy, chlorophenoxy, ethoxy, ethoxycarbonylethoxyphenoxy, benzyl, dichlorobenzyl, difluorophenyl, dichlorophenyl and morpholinyl group; and $R_2$ represents dichlorophenoxymethyl, chlorophenoxyethyl, ethoxy and methoxydichlorophenyl group.

2. A method for controlling annual and perennial weeds in a rice paddy, comprising the application to said rice paddy of an herbicidally effective amount of one or more of a compound of formula(I) as defined in claim 1.

3. An herbicidal composition comprising as an active ingredient one or more of a compound of formula(I) as defined in claim 1 and an inert carrier or diluent.

* * * * *